US009345692B2

(12) United States Patent
Qiu et al.

(10) Patent No.: US 9,345,692 B2
(45) Date of Patent: *May 24, 2016

(54) PHARMACEUTICAL FORMULATIONS: SALTS OF 8-[1-3,5-BIS-(TRIFLUOROMETHYL)PHENYL)-ETHOXY-METHYL]-8-PHENYL-1,7-DIAZA-SPIRO[4.5]DECAN-2-ONE AND TREATMENT METHODS USING THE SAME

(71) Applicant: OPKO Health, Inc., Miami, FL (US)

(72) Inventors: Zhihui Qiu, Bridgewater, NJ (US); Larisa Reyderman, Watchung, NJ (US)

(73) Assignee: OPKO Health, Inc., Miami, FL (US)

( * ) Notice: Subject to any disclaimer, the term of this patent is extended or adjusted under 35 U.S.C. 154(b) by 62 days.

This patent is subject to a terminal disclaimer.

(21) Appl. No.: 13/847,242

(22) Filed: Mar. 19, 2013

(65) Prior Publication Data

US 2014/0088128 A1    Mar. 27, 2014

Related U.S. Application Data

(60) Continuation of application No. 13/184,926, filed on Jul. 18, 2011, now Pat. No. 8,404,702, which is a continuation of application No. 12/487,263, filed on Jun. 18, 2009, now Pat. No. 7,981,905, which is a division of application No. 11/732,663, filed on Apr. 4, 2007, now Pat. No. 7,563,801.

(60) Provisional application No. 60/789,514, filed on Apr. 5, 2006.

(51) Int. Cl.
| | | |
|---|---|---|
| *A61K 31/44* | (2006.01) |
| *A61K 31/435* | (2006.01) |
| *A61K 9/16* | (2006.01) |
| *A61K 9/48* | (2006.01) |
| *A61K 31/438* | (2006.01) |

(52) U.S. Cl.
CPC ............. *A61K 31/435* (2013.01); *A61K 9/1623* (2013.01); *A61K 9/1652* (2013.01); *A61K 9/48* (2013.01); *A61K 31/438* (2013.01)

(58) Field of Classification Search
CPC ..................................................... A61K 31/44
USPC ......................................................... 514/278
See application file for complete search history.

(56) References Cited

U.S. PATENT DOCUMENTS

| | | | |
|---|---|---|---|
| 5,939,098 A | 8/1999 | Reidenberg et al. |
| 6,499,984 B1 | 12/2002 | Ghebre-Sellassie et al. |
| 7,049,320 B2 | 5/2006 | Paliwal et al. |
| 7,122,677 B2 | 10/2006 | Reichard et al. |
| 7,563,801 B2 * | 7/2009 | Qiu et al. ....................... 514/278 |
| 7,709,641 B2 | 5/2010 | Shah et al. |
| 7,902,366 B2 | 3/2011 | Paliwal et al. |
| 7,981,905 B2 * | 7/2011 | Qiu et al. ....................... 514/278 |
| 8,026,364 B2 | 9/2011 | Shah et al. |
| 8,178,550 B2 | 5/2012 | Hu et al. |
| 8,273,895 B2 | 9/2012 | Paliwal et al. |
| 8,361,500 B2 | 1/2013 | Qiu et al. |
| 8,404,702 B2 * | 3/2013 | Qiu et al. ....................... 514/278 |
| 8,470,842 B2 | 6/2013 | Hu et al. |
| 8,552,191 B2 | 10/2013 | Mergelsberg et al. |
| 8,754,216 B2 | 6/2014 | Shah et al. |
| 8,796,299 B2 | 8/2014 | Paliwal et al. |
| 2003/0158173 A1 | 8/2003 | Paliwal et al. |
| 2005/0131011 A1 | 6/2005 | Stupple |
| 2011/0038925 A1 | 2/2011 | Wan et al. |
| 2013/0122088 A1 | 5/2013 | Qiu et al. |
| 2013/0281477 A1 | 10/2013 | Hu et al. |
| 2014/0024834 A1 | 1/2014 | Mergelsberg et al. |
| 2014/0031549 A1 | 1/2014 | Wu et al. |
| 2014/0296196 A1 | 10/2014 | Palani et al. |
| 2014/0336158 A1 | 11/2014 | Paliwal et al. |

FOREIGN PATENT DOCUMENTS

| | | |
|---|---|---|
| EP | 0858341 A1 | 8/1998 |
| WO | WO 96/26726 | 9/1996 |
| WO | WO 03/051840 | 6/2003 |
| WO | WO 2005/063243 | 7/2005 |
| WO | WO-2006/007540 A1 | 1/2006 |
| WO | WO-2007/114921 A2 | 10/2007 |
| WO | WO-2007/117486 A2 | 10/2007 |
| WO | WO-2008/118328 A2 | 10/2008 |
| WO | WO-2008/118331 A2 | 10/2008 |
| WO | WO-2010/028232 A1 | 3/2010 |
| WO | WO-2011/019911 A1 | 2/2011 |

OTHER PUBLICATIONS

International Search Report, PCT/US2007/008345; mailed Jan. 22, 2008.
Noory, et al., "Steps for Development of a Dissolution Test for Sparingly Water Soluble Drug Products," *Dissolution Technologies*, Feb. 2000, Article 3.
Reddy, et al., "Novel Neurokinin-1 antagonist as antiemetics for the treatment of chemotherapy-induced emesis," *Supportive Cancer Therapy*, Apr. 1, 2006: 3(3):140-2.
Miaskkowski, et al., Cancer Pain, Nov. 2005.
U.S. Appl. No. 13/062,454, filed Mar. 4, 2011, Wu et al.
U.S. Appl. No. 14/540,635, filed Nov. 13, 2014, Qiu et al.
U.S. Appl. No. 14/683,871, filed Apr. 10, 2015, Hu et al.
Registry No. 914462-92-3, Database PROUSDDR Prous Science—Provenza 388, 08025 Barcelona, Spain, XP002454061, 2 pages, entered STN May 9, 2004, last updated Sep. 12, 2007.
King, R.E. and Schwartz, J. B., Oral Solid Dosage Forms, Chapter 90, Remington, Pharm. Sci., pp. 1603-1632 (1985).
Written Opinion for PCT/US2007/008345, 7 pages (Jan. 22, 2008).

* cited by examiner

*Primary Examiner* — Raymond Henley, III
(74) *Attorney, Agent, or Firm* — Choate, Hall & Stewart LLP; Brenda Herschbach Jarrell; Kristen C. Buteau

(57) ABSTRACT

Pharmaceutical formulations containing salts of (5S,8S)-8-[{(1R)-1-(3,5-Bis-(trifluoromethyl)phenyl]-ethoxy}-methyl]-8-phenyl-1,7-diazaspiro[4.5]decan-2-one, represented by Formula I, are disclosed. Disclosed also are methods of treatment utilizing such dosage forms.

5 Claims, 3 Drawing Sheets

PHARMACEUTICAL FORMULATIONS: SALTS OF 8-[1-3,5-BIS-(TRIFLUOROMETHYL)PHENYL)-ETHOXY-METHYL]-8-PHENYL-1,7-DIAZA-SPIRO[4.5]DECAN-2-ONE AND TREATMENT METHODS USING THE SAME

CROSS-REFERENCE TO RELATED APPLICATIONS

The present application is a continuation of U.S. application Ser. No. 13/184,926, filed Jul. 18, 2011, now issued as U.S. Pat. No. 8,404,702; which is a continuation of U.S. application Ser. No. 12/487,263, filed Jun. 18, 2009, issued as U.S. Pat. No. 7,981,905; which is a division of U.S. application Ser. No. 11/732,663, filed on Apr. 4, 2007, now issued as U.S. Pat. No. 7,563,801; which claims priority from U.S. Provisional Application 60/789,514, filed on Apr. 5, 2006.

FIELD OF THE INVENTION

This application generally relates to pharmaceutically useful formulations comprising salts of 8-[{1-(3,5-Bis-(trifluoromethyl)phenyl)-ethoxy}methyl]-8-phenyl-1,7-diaza-spiro[4.5]decan-2-one and treatment methods employing the same.

BACKGROUND OF THE INVENTION

The preparation of diazaspirodecan-2-ones named (in accordance with Bielstein nomenclature) 8-[{1-(3,5-Bis-(trifluoromethyl)phenyl)-ethoxy}methyl]-8-phenyl-1,7-diaza-spiro[4.5]decan-2-one, for example, (5S,8S)-8-[{(1R)-1-(3,5-Bis-(trifluoromethyl)phenyl)-ethoxy}methyl]-8-phenyl-1,7-diazaspiro[4.5]decan-2-one (the compound of Formula I) is disclosed in published U.S. Pat. No. 7,049,320 issued May 23, 2006 (the '320 patent), which is incorporated herein by reference in its entirety.

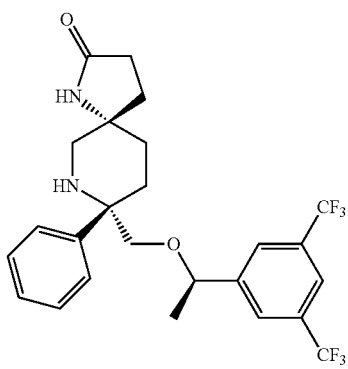

Formula I

The compounds disclosed in the '320 patent are classified as Tachykinin compounds, and are antagonists of neuropeptide neurokinin-1 receptors (the "NK-1" receptor antagonists). "NK-1" receptor antagonists have been shown to be useful therapeutic agents. For example, U.S. Pat. No. 5,760,018 (1998) describes some "NK-1" receptor antagonists as useful in the treatment of pain, inflammation, migraine and emesis (vomiting), and each of U.S. Pat. No. 5,620,989 (1997), WO 95/19344 (1995), WO 94/13639 (1994), and WO 94/10165 (1994) have described additional "NK-1" receptor antagonists which are useful in the treatment of treatment of pain, nociception and inflammation. Additional $NK_1$ receptor antagonists are described in Wu et al, Tetrahedron 56, 3043-3051 (2000); Rombouts et al, Tetrahedron Letters 42, 7397-7399 (2001); and Rogiers et al, Tetrahedron, 57, 8971-8981 (2001). Among many compounds disclosed in the abovementioned '320 patent are several novel diazaspirodecan-2-ones, including the compound of Formula I, which is believed to be useful in the treatment of nausea and emesis associated with chemotherapy treatments (Chemotherapy-induced nausea and emesis, CINE). Emesis has been a problem in chemotherapy. Chemotherapeutic agents, for example, cisplatin carboplatin and temozolomide have been associated with both acute and delayed onset nausea and vomiting. It is known to administer chemotherapeutic agents with an anti-emetic, for example, as described in U.S. Pat. No. 5,939,098, which describes coadministration of temozolomide and with ondansetron, however such therapy is not effective in preventing delayed onset nausea and vomiting.

Compounds which have been identified as having therapeutic activity must be provided in a formulation suitable for administration to a patient in need of the therapeutic properties of the compound. In general, dosage forms suitable for oral administration are preferred due to the ease of administration, negligible invasiveness of the administrative procedure, and the convenience of providing the medicament in a variety of discrete dosage sizes. In general it is preferred to provide a solid oral dosage form which administers the therapeutic agent to a recipient through the gastrointestinal tract.

OBJECTIVES AND SUMMARY OF THE INVENTION

In view of the foregoing, what is desired is a solid orally administerable dosage form containing a salt of the compound of Formula I. What is desired also is a dosage form that provides therapeutically effective serum levels of the therapeutic agent and is robust toward degradation under the environmental conditions in which it is handled and stored.

These and other objectives are provided by the present invention, which in one aspect provides a granular pharmaceutical formulation comprising a crystalline hydrochloride salt of the compound of Formula I in admixture with one or more excipients, and optionally, one or more 5HT-3 receptor antagonists, and optionally, a corticosteroid. When employed, preferably the 5HT-3 receptor antagonist is selected from Zofran (ondensetron), Kytril (granisetron), Aloxi (palonosetron), Anzemet (dolasetron), Navoban (tropisetron), and when employed, preferably the corticosteroid is selected to be dexamethasone. In some preferred embodiments the granular composition comprises crystalline hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one, lactose monohydrate, microcrystalline cellulose, croscarmellose sodium, pregelatinized starch, and magnesium stearate. In some embodiments the granular composition is contained in a gelatin capsule.

In some embodiments the pharmaceutical composition comprises a salt of (5S,8S)-8-[{(1R)-1-(3,5-Bis-(trifluoromethyl)phenyl)-ethoxy}-methyl]-8-phenyl-1,7-diazaspiro[4.5]decan-2-one selected from a hydrochloride salt and a tosylate salt. In some preferred embodiments the salt is a crystalline monohydrate hydrochloride salt having characteristic X-ray Powder Diffraction peaks present at a diffraction angle equal to those shown in Table I expressed in terms of 2θ

(all values reflect an accuracy of ±0.2), with the associated lattice "d" spacing (in angstroms) and relative peak intensities ("RI"):

TABLE I

| Diffraction angle (2θ, ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78 |

Another aspect of the present invention is the provision of a solid oral dosage in capsule form comprising 2.5 mg/dose of a crystalline hydrochloride monohydrate salt form of (5S, 8S)-8-[{(1R)-1-(3,5-Bis-(trifluoromethyl)phenyl)-ethoxy}-methyl]-8-phenyl-1,7-diazaspiro[4.5]decan-2-one (the hydrochloride monohydrate compound of Formula II),

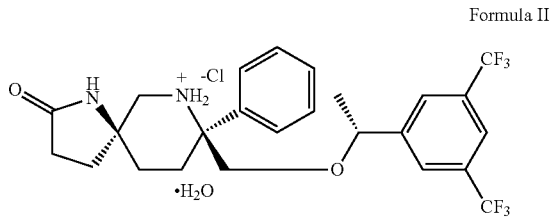

Formula II having characteristic X-ray Powder Diffraction peaks present at a diffraction angle equal to those shown in Table II, expressed in terms of 2θ (all values reflect an accuracy of ±0.2), with the associated lattice "d" spacing (in angstroms) and relative peak intensities ("RI"):

TABLE II

| Diffraction angle (2θ, ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78; | and having characteristic 12 sample average dissolution profile in 900 mL of dissolution medium comprising 0.25% sodium lauryl sulfate solution buffered with 0.05 M sodium acetate at pH 4.5 determined using a USP 2 Apparatus Paddle Stirrer with sinkers operated at 75 RPM of that shown in Table III.

TABLE III

| Time (min.) | Average (% of active initially present released) | Range of % active released over n samples |
|---|---|---|
| 5 | 69% | 64%-74% |
| 15 | 88% | 83%-94% |
| 30 | 94% | 90%-100% |
| 45 | 97% | 93%-102% |
| 60 | 98% | 94%-103% |

Another aspect of the present invention is the provision of a solid oral dosage in capsule form comprising 10.0 mg/dose of a crystalline hydrochloride monohydrate salt form of (5S, 8S)-8-[{(1R)-1-(3,5-Bis-(trifluoromethyl)phenyl)-ethoxy}-methyl]-8-phenyl-1,7-diazaspiro[4.5]decan-2-one (the hydrochloride monohydrate compound of Formula II)

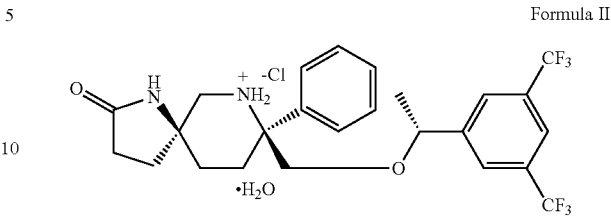

Formula II having characteristic X-ray Powder Diffraction peaks present at a diffraction angle equal to those shown in Table IV, expressed in terms of 2θ (all values reflect an accuracy of ±0.2), with the associated lattice "d" spacing (in angstroms) and relative peak intensities ("RI"):

TABLE IV

| Diffraction angle (2θ, ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78 | and having a characteristic 12 sample average dissolution profile in 900 mL of dissolution medium comprising 0.25% sodium lauryl sulfate solution buffered with 0.05 M sodium acetate at pH 4.5 determined using a USP 2 Apparatus Paddle Stirrer with sinkers operated at 75 RPM of that shown in Table V.

TABLE V

| Time (min.) | Average (% of active initially present released) | Range of % active released over n samples |
|---|---|---|
| 5 | 87% | 82%-91% |
| 15 | 95% | 91%-98% |
| 30 | 98% | 94%-100% |
| 45 | 98% | 95%-101% |
| 60 | 99% | 96%-100% |

Another aspect of the present invention is the provision of a solid oral dosage in capsule form comprising 50.0 mg/dose of a crystalline hydrochloride monohydrate salt form of (5S, 8S)-8-[{(1R)-1-(3,5-Bis-(trifluoromethyl)phenyl)-ethoxy}-methyl]-8-phenyl-1,7-diazaspiro[4.5]decan-2-one (the hydrochloride monohydrate compound of Formula II)

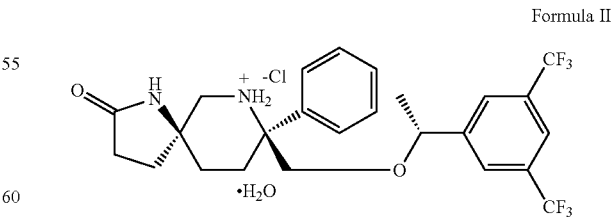

Formula II having characteristic X-ray Powder Diffraction peaks present at a diffraction angle equal to those shown in Table VI, expressed in terms of 2θ (all values reflect an accuracy of ±0.2), with the associated lattice "d" spacing (in angstroms) and relative peak intensities ("RI"):

TABLE VI

| Diffraction angle (2θ, ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78 | having a characteristic 12 sample average dissolution profile in 900 mL of dissolution medium comprising 0.25% sodium lauryl sulfate solution buffered with 0.05 M sodium acetate at pH 4.5 determined using a USP 2 Apparatus Paddle Stirrer with sinkers operated at 75 RPM of that shown in Table VII.

TABLE VII

| Time (min.) | Average (% of active initially present released) | Range of % active released over n samples |
|---|---|---|
| 5 | 88% | 74%-96% |
| 15 | 97% | 91%-101% |
| 30 | 99% | 94%-102% |
| 45 | 100% | 95%-102% |
| 60 | 100% | 96%-103% |

Another aspect of the present invention is the provision of a pharmaceutical formulation comprising a hydrochloride monohydrate salt of Formula II in a capsule oral dosage form which has a Pharmacokinetic (PK) profile obtained under single dose rising rate study conditions in accordance with Table VIII (average of eight study subjects).

TABLE VIII

| Dose (mg) | Cmax* (ng/mL) | Tmax** | AUC*** | Half Life T½ (hours) |
|---|---|---|---|---|
| 5 | 27.3 | 2 | 931 | not calc. |
| 10 | 52.7 | 2.5 | 1820 | not calc |
| 25 | 119 | 2.5 | 17200 | 183 |
| 50 | 276 | 3 | 33600 | 171 |
| 100 | 475 | 2 | 74400 | 181 |
| 200 | 944 | 4 | 148000 | 169 |

*Mean maximum plasma concentration following single administration.
**Median time (hours) of maximum plasma concentration from administration.
***Area under the plasma concentration time curve in ng hr/mL for 0 to 72 hours post administration.

The invention further provides a method of treating nausea and/or emesis. It is believed that medicament of the invention comprising salts of the compound of Formula I may be useful in the provision of anti-nausea and anti-emesis treatment for nausea and emesis arising from any cause, for example, arising from chemotherapy, from radiation therapy, arising during a post-operative recovery period, arising from motion sickness, arising from morning sickness, and arising from inner ear disturbances and infections. However, it is believed that the compound of Formula I will be most effective in the provision of anti-nausea and/or anti-emesis treatment for delayed onset nausea and/or emesis associated with chemotherapy treatments, radiation treatments, and arising during a post-operative period. In some embodiments it is preferred to coadminister an NK-1 dosage form of the invention with other therapeutic agents, for example, a chemotherapeutic agent, for example, temozolomide and cisplatin, preferably temozolomide. In some embodiments the administration of additional therapeutic agents is selected from contemporaneous administration of additional therapeutic agents contained in a separate dosage form and simultaneous administration of a dosage form containing the granulate of the present invention along with one or more therapeutic agents.

An example of contemporaneous administration is administering before, during, or after administration of a medicament comprising the granulate of the present invention, one or more additional therapeutic agents contained in one or more additional dosage forms. An example of simultaneous administration is a dosage form containing a medicament comprising multiple therapeutic agents. An example of the latter administration scheme is a capsule dosage form containing the NK-1 therapeutic agent together with one or more additional therapeutic agents, for example, a chemotherapeutic agent, for example, temozolomide. In some dosage forms containing more than one therapeutic agent it is preferred to prepare the formulation contained in the dosage form by introducing an admixture of all therapeutic agents into the formulation in place of the single drug substance, for example, the NK-1 salt of the present formulation.

In one form the therapy comprises administering a particulate form of a medicament comprising crystalline hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one (the monohydrate salt of Formula II), lactose monohydrate, microcrystalline cellulose, croscarmellose sodium, pregelatinized starch, and magnesium stearate in an amount providing a therapeutically effective serum level of the hydrochloride monohydrate salt of Formula II for the treatment and/or prevention of nausea and emesis. In the administration of such particulate medicament, preferably the particulate is contained in a capsule.

BRIEF DESCRIPTION OF THE FIGURES

FIG. 3A) and multiple day (Day 10; FIG. 3B) administration of a medicament containing a hydrochloride salt of the compound of Formula I to healthy human volunteers, horizontal axis is post administration time (hours), vertical axis is plasma concentration (ng/mL).

DETAILED DESCRIPTION OF THE INVENTION

Figure 1:
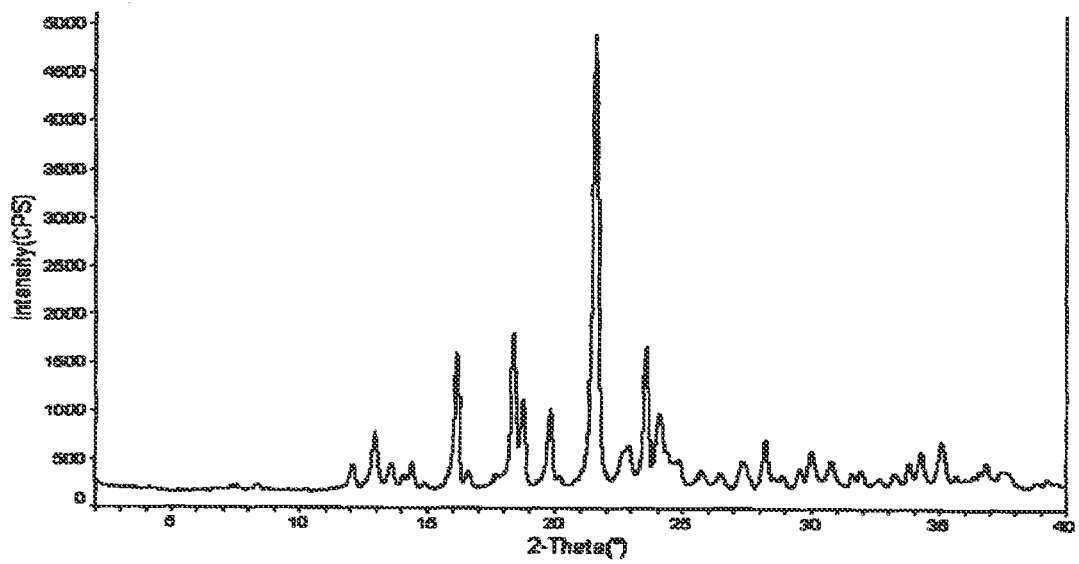
FIG. 1 presents a characteristic x-ray powder diffraction pattern of the crystalline hydrochloride monohydrate salt form of the compound of Formula I [Vertical Axis: Intensity CPS, counts (square root)); Horizontal Axis: Two Theta (degrees)].

The preparation of tachykinin compounds useful as NK-1 receptor antagonists has been described in U.S. Pat. No. 7,049,320, filed Dec. 17, 2002 (herein, the '320 patent, which is incorporated herein by reference in its entirety), including (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I).

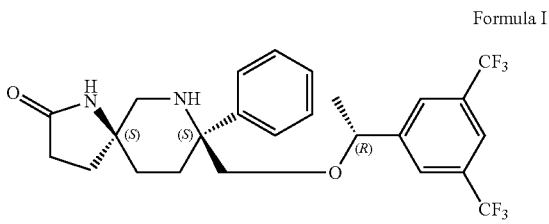

Formula I

The preparation of salts of (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I), including the monohydrate hydrochloride salt of Formula II (shown above) and various tosylate salts, having physical and chemical properties useful in the provision of medicaments are disclosed in U.S. application Nos. 60/789,280 and 60/789,513, each of which is incorporated herein in its entirety by reference.

Two of the most debilitating side effects of cytotoxic chemotherapy are nausea and vomiting (emesis). There is both acute-phase chemotherapy induced nausea and emesis (CINE) and delayed-phase CINE. Acute-phase CINE occurs in the first 24 hours after chemotherapy administration while delayed-phase CINE manifests from between 2 days and 5 days post chemotherapy administration. Acute-phase CINE has been managed by administering 5HT3 receptor antagonists, often in combination with a corticosteroid, for example, dexamethasone, this treatment has not been effective in managing delayed-phase CINE. It is believed that acute-phase CINE and delayed-phase CINE arise from different physiological phenomena. It is believed that administration of an NK-1 receptor antagonist, for example, salts of (5S,8S)-8-[{(1R)-1-(3,5-Bis-(trifluoromethyl)phenyl)-ethoxy}-methyl]-8-phenyl-1,7-diazaspiro[4.5]decan-2-one, either alone or in combination with one or more of a corticosteroid, for example, dexamethasone and/or a 5HT3 receptor antagonist, for example, ondensetron, granisetron, palonosetron, dolasetron, or tropisetron will provide a therapy effective in treatment of CINE in humans.

In general, oral dosage forms which administer a therapeutic agent to a subject through the gastrointestinal tract are desirable because such dosage forms offer ease of administration with minimal invasion of the subject receiving the therapy. Oral medicaments which are in a solid form, for example, tablets and capsules containing a particulate medicament, offer a discrete dosage form of the medicament, and provide the medicament in a form which is generally more robust in the environment in which the medicament is handled and stored in comparison to liquid dosage forms. Accordingly, it is desirable to provide medicaments containing these NK-1 receptor antagonists in a solid dosage form amenable to oral administration.

The inventors have discovered that a particulate containing a salt of (5S,8S)-8-[{(1R)-1-(3,5-Bis-(trifluoromethyl)phenyl)-ethoxy}-methyl]-8-phenyl-1,7-diazaspiro[4.5]decan-2-one (active salt) can be prepared which has useful pharmacokinetic (PK) and dissolution properties in the provision of therapy to address CINE and other conditions amenable to treatment by the administration of an NK-1 inhibitor, for example, nausea and/or emesis due to other causative factors, for example, motion sickness and morning sickness. Surprisingly, this particulate can be prepared by combining an amount of the active salt with lactose monohydrate, croscarmellose sodium, and pregelatinized starch and granulating the mixture with purified water, drying the granulate, blending the granulate with magnesium stearate and an additional amount of microcrystalline cellulose and croscarmellose sodium, and filling the resulting granulate blend into a gelatin capsule at a fill weight that provides the dosage form with the desired amount of active salt. Surprisingly, the medicament of this formulation suitably provides a serum therapeutic level of the active salt when administered orally. It is believed that this formulation, when administered in an effective dosage amount, and optionally, administered along with a separate medicament containing either a 5HT3 receptor antagonists, for example, ondensetron, granisetron, palonosetron, dolasetron, or tropisetron and/or one or more corticosteroid, for example, dexamethasone, will be useful in the management of CINE. Optionally, the formulation of the invention can additionally include one or more 5HT3 receptor antagonist, for example ondensetron, granisetron, palonosetron, dolasetron, or tropisetron, and/or one or more corticosteroid, for example, dexamethasone, in the provision of therapy in the treatment of both acute-phase and delayed-phase CINE. Whether administered as a separate medicament, or included in the formulation of the present invention, when utilized is it preferred for the 5HT3 receptor antagonist to be selected from ondensetron, granisetron, palonosetron, dolasetron, and tropisetron, and when utilized, whether as a separate medicament or included in the formulation of the present invention, it is preferred for the corticosteroid to be selected from dexamethasone.

The present formulation can also contain additional therapeutic agents, for example, chemotherapeutic agents, for example, temozolomide, providing a single medicament for administering chemotherapeutic treatment and relief and/or prevention of nausea and/or vomiting associated with such chemotherapeutic agent administration. Examples of dosage levels of temozolomide are described in U.S. Pat. No. 5,939,098 (the '098 patent), issued Aug. 17, 1999, European Patent 0858341 B1 (the '341 patent), Grant date Oct. 24, 2001, and published U.S. patent application no. 2006/0100188, published May 11, 2006 (the '188 publication). Each of the '098 patent and '341 patent describes coadministration of temozolomide with a 5HT3 inhibitor to provide therapy for immediate onset nausea and vomiting associated with chemotherapy. The '188 publication, in Tables 1 and 2 (pages 2 to 3 therein) describes detailed dosing regimens for dosing temozolomide. In some embodiments it is preferred to provide a combination of a salt of the compound of Formula I prepared in accordance with the present invention, or a pharmaceutical composition containing the salt, and other therapeutic agents, for example, a chemotherapeutic agent, for example, temozolomide and cisplatin, preferably temozolomide.

As used herein a combination includes: physically combined therapeutic agents in a pharmaceutical composition for administering in a single dosage form; a medicament or kit containing multiple therapeutic agents in one or more containers; and providing therapy that includes providing a therapeutically effective level of the compound of Formula I and other therapeutic agents, for example, by contemporaneous or simultaneous administration, as described herein, of more than one therapeutic agent. When a kit combination is provided, generally multiple medicaments are supplied in a form that will provide, upon administration to a patient in need of such therapy, a therapeutically effective amount of the active pharmaceutical ingredient(s) contained therein.

It is believed also that this medicament may be useful in the treatment of other conditions amenable to treatment by administration of an NK-1 inhibitor, including, but not limited to, cough, morning sickness, and nausea and/or vomiting arising from motion sickness.

Preferably the active salt used in the formulations of the present invention is the crystalline hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one, and a crystalline tosylate salt of (5S,8S)-8-[{(1R)-1-(3,5-Bis-(trifluoromethyl)phenyl)-ethoxy}-methyl]-8-phenyl-1,7-diazaspiro[4.5]decan-2-one, which salt has the X-ray powder diffraction pattern shown in FIG. 1. This salt has four most characteristic X-ray Powder Diffraction peaks present at a diffraction angle equal to those shown in Table IX, expressed in terms of 2θ (all values reflect an accuracy of ±0.2), with the associated lattice "d" spacing (in angstroms) and relative peak intensities ("RI"):

TABLE IX

| Diffraction angle (2θ, ± 0.2 | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78 |

In general, salts suitable for use in the formulation of the present application may be prepared in accordance with the procedures described in U.S. provisional application No. 60/789,280 entitled "HYDROCHLORIDE SALTS OF 8-[1-(3,5-Bis-(trifluoromethyl)phenyl)-ethoxymethyl]-8-phenyl-1,7-diazaspiro[4.5]decan-2-one", filed on Apr. 5, 2006, and in U.S. patent application No. 11/732,548 (now U.S. Patent No 8,178,550), filed on Apr. 4, 2007, each of which is incorporated herein by reference. Other suitable salts may be prepared in accordance with the procedures described in U.S. Provisional application No. 60/789,513 entitled "SALTS OF 8-[1-(3,5-Bis-(trifluoromethyl)phenylethoxymethyl]-8-phenyl-1,7-diazaspiro[4.5]decan-2-one AND PREPARATION PROCESS THEREFOR", filed on Apr. 5, 2006, which is incorporated herein by reference. Particularly preferred is the monohydrate hydrochloride salt of (5S,8S)-8-[{(1R)-1-(3,5-Bis-(trifluoromethyl)phenyl)-ethoxy}-methyl]-8-phenyl-1,7-diazaspiro[4.5]decan-2-one, identified therein as the monohydrate hydrochloride form 1 salt of the compound of Formula I, and depicted graphically above as the salt of Formula II.

EXAMPLES

Standard pharmaceutical manufacturing processes are utilized in the preparation of formulations of the present invention, including sieving, granulation, milling, fluid bed drying and powder mixing. For preparation of a granulate formula of the present invention these operations are carried out in accordance with the following general procedures. Blending operations are carried out in a high shear granulator manufactured by Dionsa. Granulation is carried out in the Dionsa granulator after the dry materials are blended to a homogeneous mixture. Wet milling is carried out in a Quadro Comil 197 equipped with a #5 mesh screen. Drying operations are carried out in a Strea Aeromatic T2 Fluid Bed dryer. Dry milling operations are carried out in a Quadro Comil 197 equipped with a 16 mesh screen. Blending operations are carried out in a Pharmatech Double Cone blender.

Unless noted to the contrary, all materials utilized in the formulations were articles of commerce meeting the current requirements of the United States Pharmacopeia/National Formulary (USP/NF), and active salts were obtained using the procedures in the above described in the above described in U.S. Provisional Application Nos. 60/789,280 and 60/789,513 filed concurrently on Apr. 5, 2006 which are incorporated herein by reference in their entirety, and U.S. Provisional Application No. 60/919,666, filed on Mar. 22, 2007.

X-ray powder diffraction spectroscopic analysis of hydrochloride monohydride salts was performed using a Rigaku Miniflex spectrometer, employing the following procedure. Specimens for analysis were lightly packed onto a low-background plate. The specimens were exposed to the room environment with ambient temperature and humidity. The Rigaku spectrometer was equipped with a six-plate carousel that rotated the specimen at 54 rpm, minimizing preferred orientations of the crystals in the sample studied. The Rigaku spectrometer was equipped also with a copper Kα radiation source utilized without a Kα2 filter. The spectrometer was equipped also with a variable divergence slit and 0.3 mm receiving slit. Scan range was carried out from 2.0 to 40° 2θ. Instrument calibration was verified using the Cu Kα1 peak for the 111 plane. During scanning, the step size was 0.02 degrees over step durations of 0.6 seconds. Data analysis was accomplished using Jade Plus (release 5.0.26) analysis software. The data were smoothed with a Savitzky-Golay parabolic filter at 11 points. Typically reported "d" spacing values are accurate to within ±0.4 A.

Samples preparation analysis in accordance with the above-described procedure were subjected to minimal preparation to prevent any form changes. Sample particles were lightly packed into the sample holder to insure that they formed a smooth surface and did not clump together. No solvents, drying or other preparation steps were used for other than the solvate samples prepared in accordance with the procedure described above.

Example I

Granulate Formulation

The drug substance used in the following procedure was the hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one (herein, the hydrochloride monohydrate salt) has an X-ray powder pattern shown in Figure I. The powder pattern of Figure I has four most characteristic peaks observed at 2θ=16.1 (m), 18.4 (m), 21.6 (s), and 23.5 (w)), produced in accordance with the above-referenced procedures. A granular formulation for filling into gelatin capsules containing the hydrochloride monohydrate salt for the provision of dosage forms containing the salt in an amount of 2.5 mg/dose or 10 mg/dose and 50 mg/dose was prepared in accordance with the following procedure. The weight of each of the granulate constituents used is reported below in Table XIII, which varies slightly in the amount of filler employed for each dosage strength of capsule produced from the granulate. The granulate was produced such that 300 mg of the powder provided the indicated amount of drug substance. The granulate for all dosage strengths was prepared in accordance with the following procedure.

Drug substance was hand sieved through a 600 micron screen, and the remaining excipients were screened through a 1000 micron screen prior to use. The amount of drug substance indicated in Table XIII and the amount of lactose monohydrate (impalpable grade) indicated in Table XIII as "premix" were placed into the granulator and blended for 2 minutes at an impeller speed of 133 RPM to create a uniform blend. The amount of lactose monohydrate (impalpable grade) indicated in Table XIII as "main mix", the amount of croscarmellose sodium (NF Phr. Europe) indicated in Table XIII as intergranular, and the amount of starch indicated in Table XIII were added to the granulater and blended for 2 minutes at a 133 RPM impeller speed. With the granulator operating, purified water was pumped into the dry-blended materials (up to 3600 ml at an addition rate of 75 g/min) to agglomerate the blended materials until a granulate having 32 wt. % water content was thereby formed. The wet granulate was wet-milled and sized using a conical screen mill equipped with a #5 mesh screen to provide classified wet granulate. The classified wet granulate was transferred into the fluid bed dryer and dried to a target weight of less than 3 wt. % free water (determined by loss on drying). The dried granulate was milled in the conical mill through a 16 mesh screen. The dry-milled granulate is transferred to the blender along with the weight of croscarmellose sodium indicated in Table XIII as "extragranular", and the weight of microcrystalline cellulose (Avicel PH102) indicated in Table XIII. The constituents were blended for 20 minutes at 15 RPM. The weight of magnesium stearate (Non-bovine, NF) indicated in Table XIII was screened through a 425 micron screen and added to the blender. The constituents were blended for 10 minutes at 15 RPM, and the blended formulation was discharged for encapsulation.

As mentioned above, Table XIII, which follows, shows the weights of each of the constituents used for preparing granulate which was used to fill capsules in the indicated dosage range.

TABLE XIII

| Constituent | 2.5 mg dosage | 10 mg dosage | 50 mg dosage |
| --- | --- | --- | --- |
| Active Salt | 100.0 g | 400.0 g | 1000.0 g |
| Lactose Monohydrate (premix) | 1600.0 g | 1600.0 g | 1600.0 g |
| Lactose Monohydrate (main mix) | 5560.0 g | 5260.0 g | 1030.0 g |
| Microcrystalline Cellulose | 2400.0 g | 2400.0 g | 1200.0 g |
| Pregelatinized Starch | 1800.0 g | 1800.0 g | 900.0 g |
| Croscarmellose Sodium (intergranular) | 240.0 g | 240.0 g | 120.0 g |
| Croscarmellose Sodium (extragranular) | 240.0 g | 240.0 g | 120.0 g |
| Magnesium Stearate | 60.0 g | 60.0 g | 30.0 g |

Samples of capsules filled with a granulate mixture that provides 2.5 mg, 10 mg, and 50 mg of the active salt were subjected to dissolution tests. The dissolution testing apparatus was a USP2 apparatus Paddle Stirrer filled with 900 mL of dissolution medium consisting of 0.25% sodium lauryl sulfate solution buffered with 0.05 M sodium acetate at pH 4.5. Tests were conducted at ambient temperature. The test was carried out by stabilizing the dissolution medium at the test temperature with the paddles set at 75 RPM. Test capsules are dropped into the dissolution medium with the paddles actuated. Periodically aliquot samples of the dissolution media are withdrawn and analyzed by HPLC for active content. The total amount of active present in the dissolution media is calculated based on the HPLC determination, and reported as a percentage of the total amount of active contained in the capsule introduced into the dissolution media. The results for each sample are shown below in Table X. It will be found that capsules prepared in accordance with the above-described procedure when tested under S-1 conditions as a 6 tablet average with have a Q-45 of not less than 75% with no single tablet exceeding 80%.

TABLE X

| Time (min.) | Average (% of active initially present released) | Range of % active released over n samples |
| --- | --- | --- |
| 5 | 88% | 74%-96% |
| 15 | 97% | 91%-101% |
| 30 | 99% | 94%-102% |
| 45 | 100% | 95%-102% |
| 60 | 100% | 96%-103% |

Figure 2:
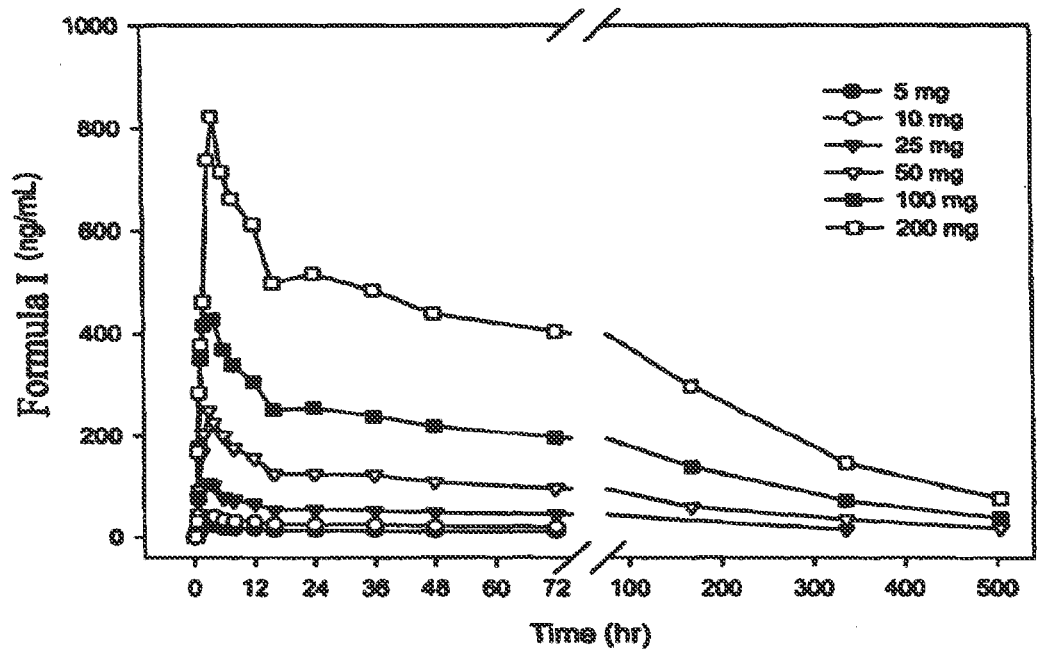
FIG. 2 presents a plasma concentration vs time profile following a single dose administration of a medicament containing a hydrochloride salt of the compound of Formula I administration to healthy human volunteers.

Single doses of the encapsulated formulation ranging from 5 mg of the active salt (2×2.5 mg capsules) to 200 mg of active salt (4×50 mg capsules) were administered to 6 cohorts each consisting of 10 healthy human volunteers, eight of whom were randomly selected to receive the active drug and two of whom were randomly selected to receive placebo. Blood samples were collected from each volunteer at predose (hour 0) and 0.25, 0.5, 0.75, 1, 1.5, 2, 3, 4, 6, 8, 12, 16, 24, 36, 48, and 72 hours. The serum drug levels of the volunteers receiving active drug are present graphically in FIG. 2. The pharmacokinetic (PK) data from this study is summarized in Table XI below.

TABLE XI

| Dose (mg) | Cmax* (ng/mL) | Tmax** | AUG*** | Half Life T½ (hours) |
| --- | --- | --- | --- | --- |
| 5 | 27.3 | 2 | 931 | not calc. |
| 10 | 52.7 | 2.5 | 1820 | not calc |
| 25 | 119 | 2.5 | 17200 | 183 |
| 50 | 276 | 3 | 33600 | 171 |
| 100 | 475 | 2 | 74400 | 181 |
| 200 | 944 | 4 | 148000 | 169 |

*Mean maximum plasma concentration following single administration.
**Median time (hours) of maximum plasma concentration from administration.
***Area under the plasma concentration time curve in nghr/mL for 0 to 72 hours post administration.

Figure 4:
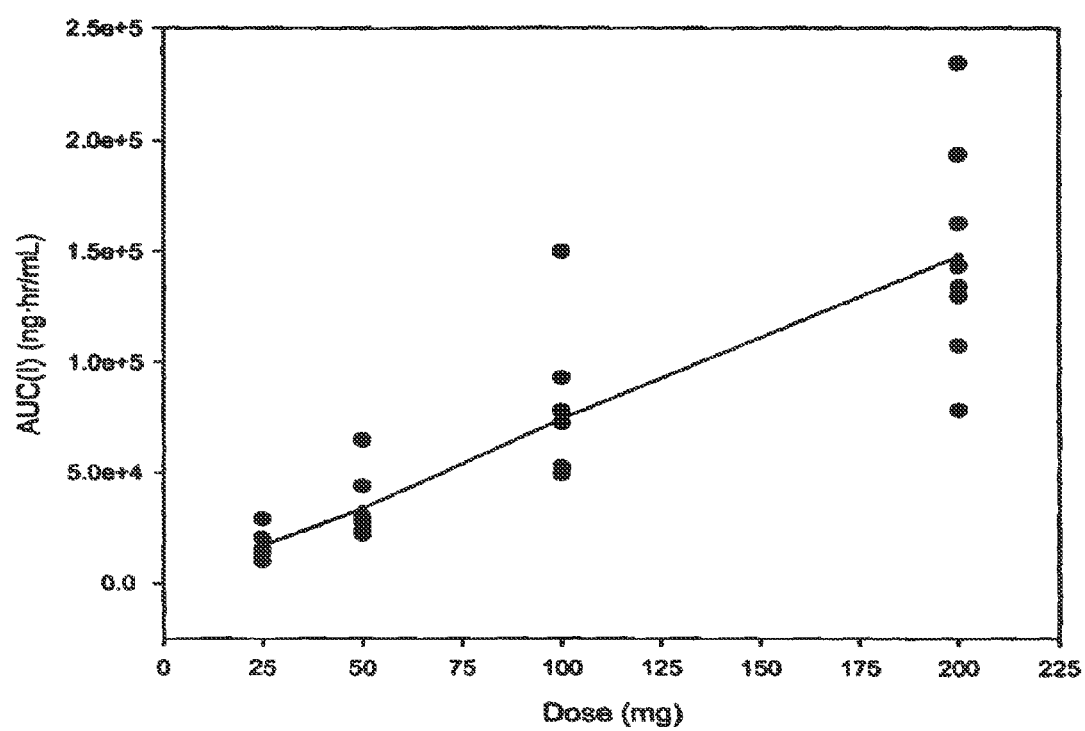
FIG. 4 presents the median and individual AUC values (area under the curve from 0 to 72 hours post single dose administration), vertical axis—AUC in ng hr/mL plasma, horizontal axis—single dose administered in mg of hydrochloride monohydrate salt of the compound of Formula I.

FIG. 4 presents the AUC data graphically, both with respect to individual data points (black circles) and statistical mean of the test group (line). These data indicate that the formulation provides the active salt in a form that is rapidly absorbed and provides increasing exposure of the active in a dose-related manner.

Figure 3A:
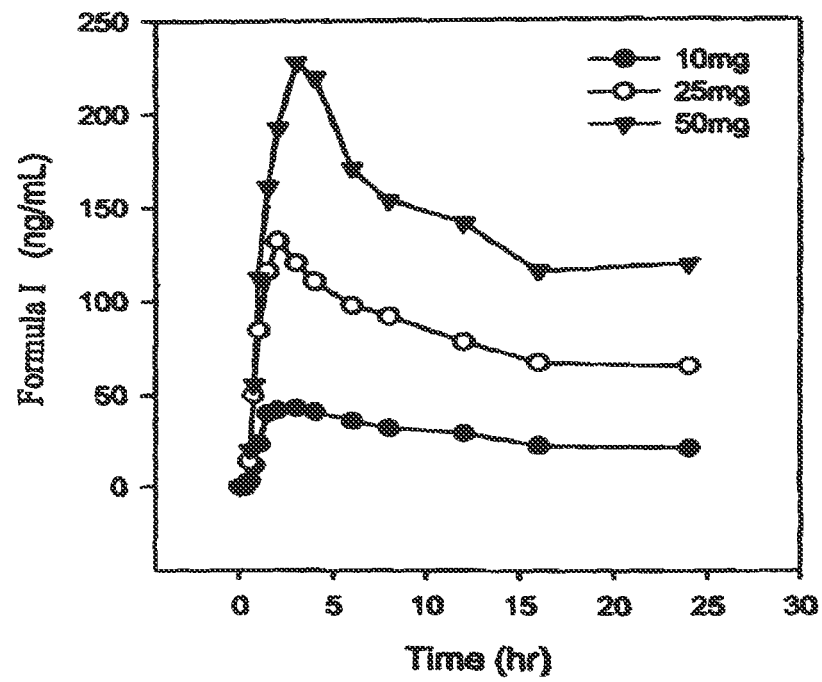
FIGS. 3A and 3B present a pharmacokinetic profile showing the plasma concentration vs time following a single day (Day 1.
Figure 3B:
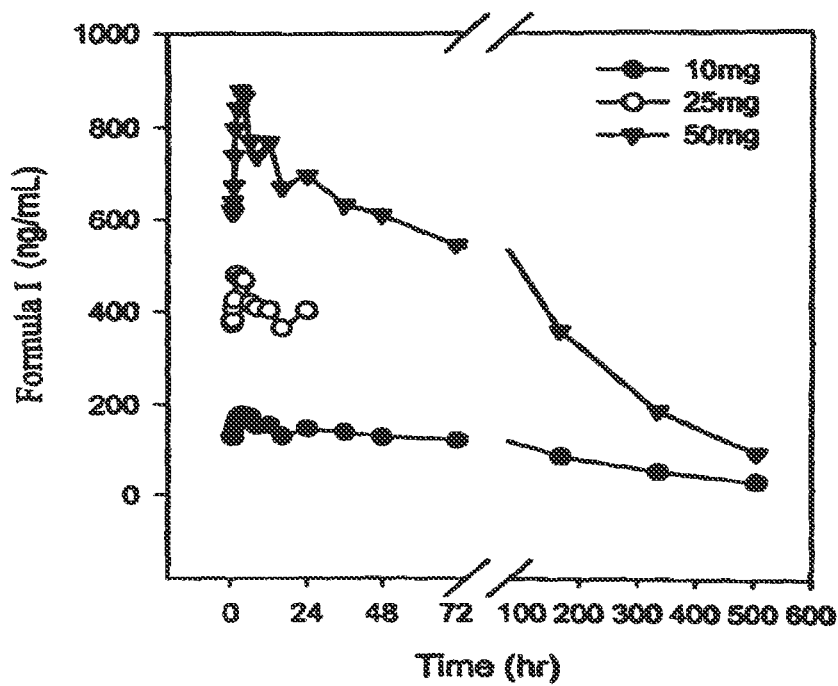

In a second study, three cohorts of 8 healthy volunteers each were administered 10, 25, or 50 mg per day for each of 10 days. Administration in every case followed a 10 hour fast. Blood samples were collected from each volunteer at predose (hour 0) and 0.25, 0.5, 0.75, 1, 1.5, 2, 3, 4, 6, 8, 12, 16, 24, 36, 48, and 72 hours on each of days 1 and 10. The results of this study are present graphically in FIGS. 3A (day 1) and 3B (day 10), and summarized in Table XII below.

TABLE XII

| Dose | Cmax* (ng/mL) | Tmax** | AUC*** | Half Life T½ (hours) |
| --- | --- | --- | --- | --- |
| Day 1 Data | | | | |
| 10 mg | 48.6 | 3 | 673 | not calc. |
| 25 mg | 139 | 2 | 1950 | not caic |
| 50 mg | 254 | 3 | 3400 | not caic |
| Day 10 Data | | | | |
| 10 mg | 180 | 3 | 3590 | 238 |
| 25 mg | 491 | 2 | 9720 | not calc. |
| 50 mg | 895 | 2.5 | 17700 | 172 |

*Mean maximum plasma concentration following single administration.
**Median time (hours) of maximum plasma concentration from administration.
***Area under the plasma concentration time curve in ng · hr/mL for 0 to 72 hours post administration.

These data show that the active is rapidly absorbed and that exposure increases with increasing dose. The half-life is independent of dose and consistent with that observed from the single dose studies. Accumulation is consistent with the long half life of the active and is approximately 5-fold of the single dose.

What is claimed is:

1. A method of treating nausea and/or emesis in a mammal comprising administering to the mammal a pharmaceutical formulation comprising a crystalline tosylate salt of (5S,8S)-8-[{(1R)-1-(3,5-bis-(trifluoromethyl)phenyl]-ethoxy}-methyl]-8-phenyl-1,7-diazaspiro[4,5]decan-2-one, and a pharmaceutically acceptable excipient, and wherein said nausea and/or emesis arises from chemotherapy, radiation therapy, motion sickness, morning sickness, or inner ear disturbances and infections, or wherein said nausea and/or emesis arises during a post-operative recovery period.

2. The method according to claim 1 wherein the pharmaceutically acceptable excipient is selected from at least one of the group consisting of lactose, microcrystalline cellulose, croscarmellose sodium, pregelantinized starch, and magnesium stearate.

3. The method of claim 1 wherein the formulation is a granular formulation.

4. The method of claim 1 wherein the amount of active ingredient ranges from 5-200 mg per dosage form.

5. The method of claim 1 wherein the dosage form contains 200 mg of the crystalline tosylate salt (5S,8S)-8-[{(1R)-I-(3,5-Bis-(trifluoromethyl)pheny]-ethoxy}-methyl]-8-phenyl-1,7-diazaspiro[4.5]decan-2-one.

* * * * *